US006794405B2

(12) United States Patent
Rong et al.

(10) Patent No.: US 6,794,405 B2
(45) Date of Patent: Sep. 21, 2004

(54) ALICYCLIC IMIDAZOLES AS $H_3$ AGENTS

(75) Inventors: Yajing Rong, Beachwood, OH (US); Jack B. Jiang, Orange Village, OH (US); Syed M. Ali, Solon, OH (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/344,787

(22) PCT Filed: Aug. 15, 2001

(86) PCT No.: PCT/US01/41738

§ 371 (c)(1), (2), (4) Date: Aug. 4, 2003

(87) PCT Pub. No.: WO02/13821

PCT Pub. Date: Feb. 21, 2002

(65) Prior Publication Data

US 2004/0029943 A1 Feb. 12, 2004

Related U.S. Application Data

(60) Provisional application No. 60/225,968, filed on Aug. 17, 2000.

(51) Int. Cl.[7] ................. A61K 31/4164; C07D 233/64
(52) U.S. Cl. .................................... 514/396; 548/345.1
(58) Field of Search ....................... 548/345.1; 514/396

(56) References Cited

U.S. PATENT DOCUMENTS

| | | | | |
|---|---|---|---|---|
| 3,940,484 A | * | 2/1976 | Baker et al. ............. | 514/235.8 |
| 3,996,366 A | | 12/1976 | Baker et al. ............... | 424/273 |
| 4,767,778 A | | 8/1988 | Arrang et al. .............. | 514/397 |
| 5,217,986 A | | 6/1993 | Pomponi et al. ........... | 514/400 |
| 5,498,722 A | * | 3/1996 | Ross et al. ................ | 548/315.4 |
| 5,559,113 A | | 9/1996 | Schwartz et al. ........... | 514/252 |
| 5,652,258 A | | 7/1997 | Phillips et al. ............. | 514/400 |
| 5,990,317 A | | 11/1999 | Phillips et al. ........... | 548/338.1 |
| 6,008,240 A | | 12/1999 | Phillips et al. ............. | 514/400 |

FOREIGN PATENT DOCUMENTS

| | | |
|---|---|---|
| WO | WO 92/15567 A1 | 9/1992 |
| WO | WO 93/12107 A1 | 6/1993 |
| WO | WO 96/38141 A1 | 12/1996 |
| WO | WO 96/38142 A1 | 12/1996 |
| WO | WO 96/40126 A1 | 12/1996 |

OTHER PUBLICATIONS

CA Registry No. 218273–93–9, entry date in Registry file—Jan. 28, 1999.*
Tedford et al., Journal of Pharmacology and Experimental Therapeutics (May 1999), 289(2), pp. 1160–1168.*
Ali et al., Journal of Medicinal Chemistry (Mar. 11, 1999), 42(5), pp. 903–909.*
Judd et al., Journal of Medicinal Chemistry (1994), 37(19), pp. 3108–3120.*
Dereu et al., CA 102:24618, 1985.*
Baker et al., CA 79:53327, 1973.*
Burger, CA 77:109198, 1972.*
Burger et al., Journal of Medicinal Chemistry (1970), 13(1), pp. 33–35.*
Vongeldern et al., CA 123:257412, 1995.*
Weinstock, CA 122:187590, 1995.*
Nasu et al., CA 110: 192824, 1989.*
Harper et al., British Journal of Pharmacology (Oct. 1999), 128(3), pp. 751–759.*
Schubert et al., CA 58:4542c, 1963.
De Esch et al., J. Medicinal Chemistry, vol. 42, No. 7, pp. 1115–1122, Apr. 8, 1999.

* cited by examiner

*Primary Examiner*—Laura L. Stockton
(74) *Attorney, Agent, or Firm*—J. Eric Thies; Melvin Winokur

(57) ABSTRACT

Alicyclic imidazole compounds; pharmaceutically active compositions containing such compounds; and the use of such compounds in formulations for the control or prevention of disease states in which histamine $H_3$ receptors are involved, such as allergy, inflammation, hypotension, glaucoma, sleeping disorders, states of hyper- and hypo-motility of the gastro-intestinal tract, cardiovascular disease, hypo- and hyper-activity of the central nervous system, Alzheimer's, schizophrenia, obesity and migraines are disclosed.

3 Claims, No Drawings

ALICYCLIC IMIDAZOLES AS H₃ AGENTS

CROSS REFERENCE RELATED APPLICATIONS

This application is a U.S. National Phase application under 35 U.S.C. § 371 of PCT Application No. PCT/US01/41738, filed Aug. 15, 2001, which claims priority under 35 U.S.C. § 119 from U.S. application Ser. No. 60/225,968 filed Aug. 17, 2000.

FIELD OF THE INVENTION

The present invention is directed to alicyclic imidazoles which interact with the histamine $H_3$ receptor as agonists, antagonists or inverse agonists; pharmaceutically active compositions containing such compounds; and the use of such compounds in formulations for the control or prevention of disease states in which histamine $H_3$ receptors are involved, such as allergy, inflammation, hypotension, glaucoma, sleeping disorders, states of hyper- and hypo-motility of the gastro-intestinal tract, cardiovascular disease, hypo- and hyper-activity of the central nervous system, Alzheimer's, schizophrenia, obesity and migraines.

BACKGROUND OF THE INVENTION

Histamine plays a role in regulating attentiveness and cognition in the central nervous system (CNS), and histamine levels in the brain are controlled by the histamine $H_3$ receptor. Moreover, serotonin, norepinephrine, dopamine and acetylcholine all have been demonstrated to be regulated by the histamine $H_3$ receptor. These neurotransmitters are known to play a role in many CNS psychiatric disorders involving higher cognitive function and/or emotion, Consequently, compounds affecting $H_3$ receptor function (as agonists, antagonists or inverse agonists) could have utility in the treatment of a variety of CNS maladies, including but not limited to dementias, attention deficit hyperactivity disorder, depression, anxiety and schizophrenia.

Histamine is also involved in the control of sleep/wake states and appetite. Accordingly, histamine $H_3$ receptor ligands might be expected to be useful in treating insomnia, narcolepsy, age-related sleep disorders, obesity and anorexia. Although they exist in low density outside of the brain, histamine $H_3$ receptors are found on the sympathetic and parasympathetic nerve terminals in the periphery, including the vasculature and heart. Thus, compounds that alter histamine $H_3$ receptor activity might also have clinical utility in treating conditions such as migraine and cardiac dysfunction.

Various imidazole-containing compounds are disclosed in WO 92/15567, WO 93/12107, and U.S. Pat. Nos. 5,217,986 and 5,559,113. 2-(4-imidazolyl)cyclopropylamine is disclosed in U.S. Pat. No. 4,767,778. 1H-4(5)-substituted imidazole derivatives are disclosed in WO 96/38142 and U.S. Pat. No. 6,072,057. 2-(1H-4(5)-imidazoyl)cyclopropyl derivatives are disclosed in U.S. Pat. Nos. 6,008,240; 5,990, 317 and 5,652,258. However, there is still a need for novel, histamine H, receptor-active imidazoyl cyclopropyl derivatives.

BRIEF SUMMARY OF THE INVENTION

The present invention is directed to alicyclic imidazoles which interact with the histamine $H_3$ receptor as agonists, antagonists or inverse agonists; pharmaceutically active compositions containing such compounds; and the use of such compounds in formulations for the control or prevention of disease states in which histamine $H_3$ receptors are involved, such as allergy, inflammation, hypotension, glaucoma, sleeping disorders, states of hyper- and hypo-motility of the gastro-intestinal tract, cardiovascular disease, hypo- and hyper-activity of the central nervous system, Alzheimer's, schizophrenia, obesity and migraines.

The invention is directed to novel compounds of Formula I as follows:

Formula I

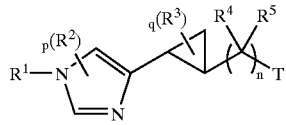

wherein n is an integer of zero to six;

p is an integer of zero to two;

q is an integer of zero to four;

T is selected from the group consisting of $-NR^6R^7$, $-N(R^8)C(NR^9)R^{10}$, $-CN$, $-OH$, $-H$, $-OR^{11}$, $-OC(O)R^{12}$, $-C(O)R^{13}$, $-C(O)NH_2$, $-C(N-OH)H$, $-SC(S)R^{14}$, $-NR^{15}C(S)R^{16}$, $-NR^{17}C(O)R^{18}$, $-SC(NR^{19})R^{20}$, $-OC(NR^{21})R^{22}$, $R^{23}$, $-N(R^{24})C(O)N(R^{25})$, $-N(R^{26})C(O)$, and $-O(O)NR^{27}R^{28}$;

$R^1$ is selected from the group consisting of hydrogen, hydroxyl, alkyl, alkenyl, alkynyl, alkoxy, alkenoxy, alkynoxy, thioalkoxy, hydroxyalkyl, aliphatic acyl, $-CF_3$, $-N(C_1-C_3$ alkyl)$-C(O)(C_1-C_3$ alkyl), $-NHC(O)NH(C_1-C_3$ alkyl), $-NHC(O)N(C_1-C_3$ alkyl)$C(O)NH(C_1-C_3$ alkyl), $-C_1-C_3$ alkylamino, alkenylamino, alkynylamino, di($C_1-C_3$ alkyl)amino, $-C(O)O-(C_1-C_3$ alkyl), $-C(O)NH-(C_1-C_3$ alkyl), $-CH=NOH$, $-PO_3H_2$, $-OPO_3H_2$, $-C(O)N(C_1-C_3$ alkyl)$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, $-SO_2-(C_1-C_3$ alkyl), $-SO_3-(C_1-C_3$ alkyl), sulfonamido, aryloxyalkyl, carboxyl, carbamate and $-C(O)NH($benzyl$)$; and $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are each independently selected from the group consisting of hydrogen, halogen, hydroxyl, alkyl, alkenyl, alkynyl, alkoxy, alkenoxy, alkynoxy, thioalkoxy, hydroxyalkyl, aliphatic acyl, $-CF_3$, $-NO_2$, amino, $-CN$, carboxy, $-N(C_1-C_3$ alkyl)$-C(O)(C_1-C_3$ alkyl), $-NHC(O)NH(C_1-C_3$ alkyl), $-NHC(O)N(C_1-C_3$ alkyl)$C(O)NH(C_1-C_3$ alkyl), $-C_1-C_3$ alkylamino, alkenylamino, alkynylamino, di($C_1-C_3$ alkyl)amino, $-C(O)O-(C_1-C_3$ alkyl), $-C(O)NH-(C_1-C_3$ alkyl), $-CH=NOH$, $-PO_3H_2$, $-OPO_3H_2$, $-C(O)N(C_1-C_3$ alkyl)$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, $-SO_2-(C_1-C_3$ alkyl), $-SO_3-(C_1-C_3$ alkyl), sulfonamido, aryloxyalkyl, carboxyl, carbamate and $-C(O)NH($benzyl$)$;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are unsubstituted or substituted with at least one electron donating or electron withdrawing group; and pharmaceutically acceptable salts thereof;

with the proviso that when T is —NR$^6$R$^7$, R$^1$ is hydrogen and n is zero, R$^6$ and R$^7$ are not both hydrogen;

and the proviso that when T is —OH, n is one, R$^4$ and R$^5$ are each hydrogen, and p and q are zero, R$^1$ is not triphenylmethyl;

and the proviso that when T is —C(O)R$^{13}$ and n is zero, R$^{13}$ is not hydrogen or a chiral moiety.

For compounds of Formula I, n may be an integer of zero to three; R$^1$ may be hydrogen, R$^2$, R$^3$, R$^4$ and R$^5$ may each independently be hydrogen, halogen, hydroxyl, lower alkyl, alkenyl, alkynyl or aryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ may each be hydrogen, lower alkyl, alkenyl, alkynyl, aryl and heterocyclyl. Presently preferred compounds of Formula I have T as —N(R$^8$)C(NR$^9$)R$^{10}$, —OC(O)R$^{12}$, —C(O)R$^{13}$, —C(O)NH$_2$, —C(N—OH)H, —SC(S)R$^{14}$, —NR$^{15}$C(S)R$^{16}$, —NR$^{17}$C(O)R$^{18}$, —SC(NR$^{19}$)R$^{20}$ or —OC(NR$^{21}$)R$^{22}$ when n is zero or T as —NR$^6$R$^7$, —CN, —OH, —H, —OR$^{11}$ or R$^{23}$ when n is one.

More specifically, the compounds of this invention may be described by Formula II below

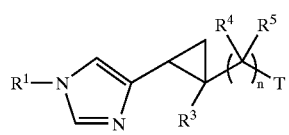

Formula II wherein n is an integer of zero to three;

T is selected from the group consisting of —NR$^6$R$^7$, —N(R$^8$)C(NR$^9$)R$^{10}$, —CN, —OH, —H, —OR$^{11}$, —OC(O)R$^{12}$, —C(O)R$^{13}$, —C(O)NH$_2$, —C(N—OH)H, —SC(S)R$^{14}$, —NR$^{15}$C(S)R$^{16}$, —NR$^{17}$C(O)R$^{18}$, —SC(NR$^{19}$)R$^{20}$, —OC(NR$^{21}$)R$^{22}$ and R$^{23}$;

R$^1$ is selected from the group consisting of hydrogen, hydroxyl, alkyl, alkenyl, alkynyl, alkoxy, alkenoxy, alkynoxy, thioalkoxy, hydroxyalkyl, aliphatic acyl, —CF$_3$, —N(C$_1$-C$_3$ alkyl)—C(O)(C$_1$-C$_3$ alkyl), —NHC(O)NH(C$_1$-C$_3$ alkyl), —NHC(O)N(C$_1$-C$_3$ alkyl)C(O)NH(C$_1$-C$_3$ alkyl), —C$_1$-C$_3$ alkylamino, alkenylamino, alkynylamino, di(C$_1$-C$_3$ alkyl)amino, —C(O)O—(C$_1$-C$_3$ alkyl), —C(O)NH—(C$_1$-C$_3$ alkyl), —CH=NOH, —PO$_3$H$_2$, —OPO$_3$H$_2$, —C(O)N(C$_1$-C$_3$ alkyl)$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, aryloxyalkyl, carboxyl, carbamate and —C(O)NH(benzyl); and R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are each independently selected from the group consisting of hydrogen, halogen, hydroxyl, alkyl, alkenyl, alkynyl, alkoxy, alkenoxy, alkynoxy, thioalkoxy, hydroxyalkyl, aliphatic acyl, —CF$_3$, —NO$_2$, amino, —CN, carboxy, —N(C$_1$-C$_3$ alkyl)-C(O)(C$_1$-C$_3$ alkyl), —NHC(O)NH (C$_1$-C$_3$ alkyl), —NHC(O)N(C$_1$-C$_3$ alkyl)C(O)NH (C$_1$-C$_3$ alkyl), —C$_1$-C$_3$ alkylamino, alkenylamino, alkynylamino, di(C$_1$-C$_3$ alkyl)amino, —C(O)O—(C$_1$-C$_3$ alkyl), —C(O)NH—(C$_1$-C$_3$ alkyl), —CH=NOH, —PO$_3$H$_2$, —OPO$_3$H$_2$, —C(O)N(C$_1$-C$_3$ alkyl)$_2$, haloalkyl, alkoxyalkoxy, carboxaldehyde, carboxamide, cycloalkyl, cycloalkenyl, cycloalkynyl, cycloalkylalkyl, aryl, aroyl, aryloxy, arylamino, biaryl, thioaryl, diarylamino, heterocyclyl, alkylaryl, aralkenyl, aralkyl, alkylheterocyclyl, heterocyclylalkyl, sulfonyl, —SO$_2$—(C$_1$-C$_3$ alkyl), —SO$_3$—(C$_1$-C$_3$ alkyl), sulfonamido, aryloxyalkyl, carboxyl, carbamate and —C(O)NH(benzyl);

wherein R$^1$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are unsubstituted or substituted with at least one electron donating or electron withdrawing group;

and pharmaceutically acceptable salts thereof;

with the proviso that when T is —NR$^6$R$^7$, R$^1$ is hydrogen and n is zero, R$^6$ and R$^7$ are not both hydrogen;

and the proviso that when T is —OH, n is one, and R$^4$ and R$^5$ are each hydrogen, R$^1$ is not triphenylmethyl;

and the proviso that when T is —C(O)R$^{13}$ and n is zero, R$^{13}$ is not hydrogen or a chiral moiety.

For presently preferred compounds of Formula II, R$^1$ may be hydrogen; R$^3$ may be hydrogen or lower alkyl; R$^4$ and R$^5$ may each be hydrogen, halogen, hydroxyl, lower alkyl, alkenyl, alkynyl or aryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ may each be hydrogen, lower alkyl, alkenyl, alkynyl, aryl or heterocyclyl. Presently preferred compounds of Formula II have T as —N(R$^8$)C(NR$^9$)R$^{10}$, —OC(O)R$^{12}$, —C(O)R$^{13}$, —C(O)NH$_2$, —C(N—OH)H, —SC(S)R$^{14}$, —NR$^{15}$C(S)R$^{16}$, —NR$^{17}$C(O)R$^{18}$, —SC(NR$^{19}$)R$^{20}$ or —OC(NR$^{21}$)R$^{22}$ when n is zero or T as —NR$^6$R$^7$, —CN, —OH, —H, —OR$^{11}$ or R$^{23}$ when n is one.

More specifically, the compounds of this invention may be described by Formula III below

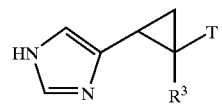

Formula III wherein T is selected from the group consisting of —N(R$^8$)C(NR$^9$)R$^{10}$, —OC(O)R$^{12}$, —C(O)R$^{13}$, —C(O)NH$_2$, —C(N—OH)H, —SC(S)R$^{14}$, —NR$^{15}$C(S)R$^{16}$, —NR$^{17}$C(O)R$^{18}$, —SC(NR$^{19}$)R$^{20}$ and —OC(NR$^{21}$)R$^{22}$;

R$^3$ is selected from the group consisting of hydrogen and lower alkyl; and,

R$^8$, R$^9$, R$^{10}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are each independently selected from the group consisting of hydrogen, lower alkyl, alkenyl, alkynyl, aryl and heterocyclyl;

wherein R$^3$, R$^8$, R$^9$, R$^{10}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ are unsubstituted or substituted with at least one electron donating or electron withdrawing group;

and pharmaceutically acceptable salts thereof;

with the proviso that when T is —C(O)R$^{13}$, R$^{13}$ is not hydrogen or a chiral moiety.

More specifically, the compounds of this invention may be described by Formula IV below

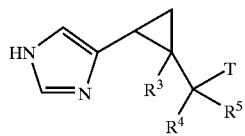

Formula IV wherein T is selected from the group consisting of —$NR^6R^7$, —CN, —OH, —H, —$OR^{11}$ and $R^{23}$;

$R^3$ is selected from the group consisting of hydrogen and methyl;

$R^4$ and $R^5$ are each independently selected from the group consisting of hydrogen, halogen, hydroxyl, lower alkyl, alkenyl, alkynyl and aryl; and, $R^6$, $R^7$, $R^{11}$ and $R^{23}$ are each independently selected from the group consisting of hydrogen, lower alkyl, alkenyl, alkynyl, aryl and heterocyclyl;

wherein $R^3$, $R^4$, $R^5$, $R^6$, $R^7$, $R^{11}$ and $R^{23}$ are unsubstituted or substituted with at least one electron donating or electron withdrawing group;

and pharmaceutically acceptable salts thereof.

Formulae I–IV also encompass esters, carbamates, aminals, amides, optical isomers or pro-drugs thereof.

Presently preferred compounds include 4-(trans-2-cyano-cyclopropyl)imidazole, 4-(trans-2-aminocarbonyl-cyclopropyl)imidazole, 4-(trans-2-amidino-cyclopropyl)imidazole, 4-(trans-2-aminomethyl-cyclopropyl)imidazole, 4-(trans-2-N-hydroxyimino-cyclopropyl)imidazole, 4-(trans-2-hydroxymethyl-cyclopropyl)imidazole, 4-(trans-2-N-methylamidino-cyclopropyl)imidazole, 4-(trans-2-aminomethyl-2-methyl-cyclopropyl)imidazole, 4-(trans-2-amidino-2-methyl-cyclopropyl)imidazole and pharmaceutically acceptable salts thereof. The present invention also relates to pharmaceutical compositions comprising a physiologically acceptable diluent and at least one compound of the present invention; and a method for regulation of histamine $H_3$ receptors in a mammal by agonism, antagonism, or inverse agonism of said receptors, comprising administering to a mammal in need of such regulation a therapeutic amount of a compound of the present invention.

DETAILED DESCRIPTION OF THE INVENTION

Definitions of Terms

The term "alkyl" as used herein, alone or in combination, refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "aliphatic acyl" as used herein, alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. "Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like. The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy" as used herein, alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy" as used herein, alone or in combination, refers to a radical of formula alkynyl-O—, provided that the radical is not an -ynol ether.

Examples of suitable alkynoxy radicals include, but are not limited to, propargyloxy, 2-butynyloxy and the like.

The term "carboxyl" as used herein refers to a carboxylic acid radical, —C(O)OH.

The term "carboxy" as used herein refers to —C(O)—.

The term "thioalkoxy" refers to a thioether radical of formula alkyl-S—, wherein "alkyl" is as defined above.

The term "carboxaldehyde" as used herein refers to —C(O)R wherein R is hydrogen.

The terms "carboxamide" or "amide" as used herein refer to —C(O)NR$_a$R$_b$ wherein R$_a$ and R$_b$ are each independently hydrogen, alkyl or any other suitable substituent.

The term "alkoxyalkoxy" as used herein refers to R$_c$O—R$_d$O— wherein R$_c$ is lower alkyl as defined above and R$_d$ is alkylene wherein alkylene is —(CH$_2$)$_{n'}$— wherein n' is an integer from 1 to 6. Representative examples of alkoxyalkoxy groups include methoxymethoxy, ethoxymethoxy, t-butoxymethoxy among others.

The term "alkylamino" as used herein refers to R$_c$NH— wherein R$_c$ is a lower alkyl group, for example, ethylamino, butylamino, among others.

The term "alkenylamino", as used herein, alone or in combination, refers to a radical of formula alkenyl-NH- or (alkenyl)$_2$N—, wherein the term "alkenyl" is as defined above, provided that the radical is not an enamine. An example of such alkenylamino radical is the alkylamino radical.

The term "alkynylamino" as used herein, alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to R$_f$R$_g$N— wherein R$_f$ and R$_g$ are independently selected from lower alkyl, for example diethylamino, and methyl propylamino, among others.

The term "amino" as used herein refers to H$_2$N—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, triphenylmethyl, pyridylmethyl, tetrazolyl methyl, furylmethyl, imidazolyl methyl, indolylmethyl, thienylpropyl and the like.

The term "aralkenyl" as used herein, alone or in combination, refers to an aryl substituted alkenyl radical, wherein the terms "aryl" and "alkenyl" are as defined above.

The term "arylamino" as used herein, alone or in combination, refers to a radical of formula aryl-NH—, wherein "aryl" is as defined above. Examples of arylamino radicals include, but are not limited to, phenylamino (anilido), naphthlamino, 2-, 3-, and 4-pyridylamino and the like.

The term "biaryl" as used herein, alone or in combination, refers to a radical of formula aryl-aryl, wherein the term "aryl" is as defined above.

The term "thioaryl" as used herein, alone or in combination, refers to a radical of formula aryl-S—, wherein the term "aryl" is as defined above. An example of a thioaryl radical is the thiophenyl radical.

The term "aroyl" as used herein, alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to a hemi-acetal of the structure R$_h$C(NR$_i$R$_j$)(NR$_k$R$_l$)— wherein R$_h$, R$_i$, R$_j$, R$_k$ and R$_l$ are each independently hydrogen, alkyl or any other suitable substituent The term "ester" as used herein refers to —C(O)R$_m$, wherein R$_m$ is hydrogen, alkyl or any other suitable substituent.

The term "carbamate" as used herein refers to compounds based on carbamic acid, NH$_2$C(O)OH.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in

*Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

"Chiral moieties" as used herein refers to substituents having a chiral center.

"Sulfonamido" as used herein refers to —SO$_2$NH$_2$.

Abbreviations

Abbreviations which have been used in the schemes and the examples which follow are: LAH for lithium aluminum hydride, TFA for trifluoroacetic acid and EDTA for ethylene diamine tetraacetic acid.

A detailed description of the preparation of representative compounds of the present invention is set forth in the Examples.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammoniun among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifing agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The present invention contemplates both synthetic compounds of Formulae I–IV of the present invention, as well as compounds formed by in vivo conversion to compounds of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Compounds of Formula I may be prepared according to the syntheses depicted in Scheme I below.

Scheme I

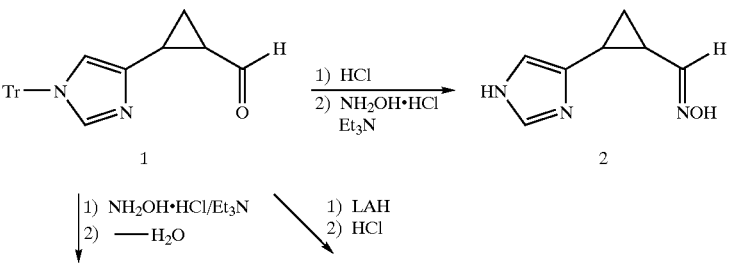

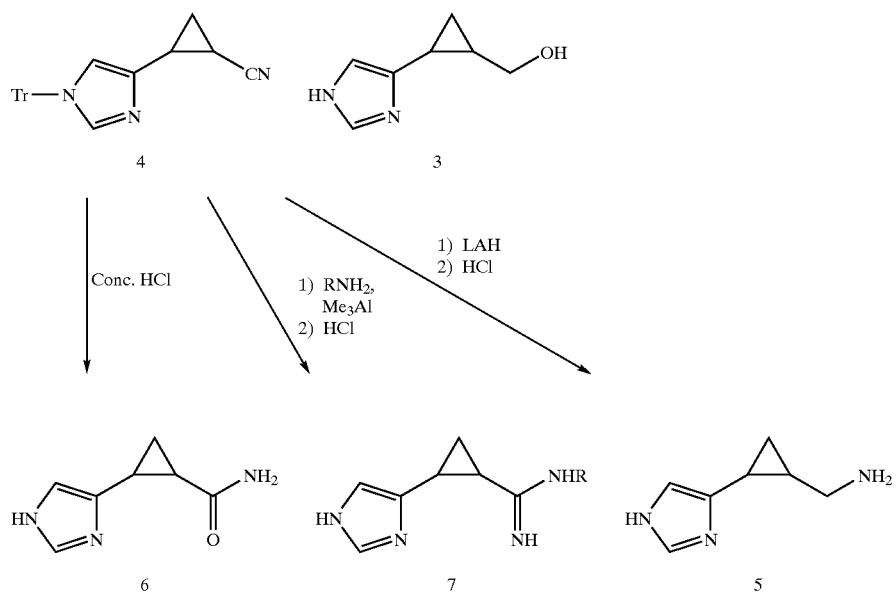

The aldehyde 1 was prepared according to a procedure described in Phillips et al., U.S. Pat. No. 6,008,240. Using aldehyde 1 as the starting material, a number of compounds of Formula I may be prepared. For example, the oxime cyclopropyl imidazole 2 was synthesized from aldehyde 1 by removing the trityl protective group using HCl followed by treatment with hydroxyamine, and alcohol 3 was obtained by reducing aldehyde 1.

When treated with hydroxyamine without removing the protective group followed by dehydration, the aldehyde 1 gave rise to the nitrile 4, which upon reduction furnished the aminomethyl product 5. The nitrile 4 was also converted to the amidine 7, using alkylaluminal in the presence of an amine. In addition, hydrolysis of the nitrile 4 under acidic conditions afforded amide 6.

The following Examples are presented to describe preferred embodiments and utilities of the invention and are not meant to limit the invention unless otherwise stated in the claims appended hereto.

Example 1

Preparation of N-triphenylmethyl-4-(trans-2-cyano-cyclopropyl)imidazole

To a solution of hydroxylamine hydrochloride (816 mg, 12 mmol) in anhydrous acetonitrile (35 mL), were added triethylamine (1.6 ml, 12 mmol), and 2-[1-(triphenylmethyl)imidazol-4-yl]cyclopropanecarbaldehyde (4.0 g, 11 mmol) The resulting mixture was stirred for about 2 hours followed by the addition of phthalic anhydride (1.6 g, 11 mmol) under nitrogen. Then the reaction mixture was heated under reflux for 8 hours, concentrated under reduced pressure, diluted with 5% aqueous ammonia (30 mL), and extracted with ethyl acetate (3×40 ml). The organic layer was dried with $MgSO_4$, and then evaporated under reduced pressure. The resulting residue was purified on a silica gel column using ethyl acetate/hexane (v/v:1/6) as the eluting solvent to give the title compound as a pale yellow solid (2.4 g, 64% yield).

Preparation of 4-(trans-2-cyano-cyclopropyl)imidazole trifluoroacetic acid salt

A mixture of N-triphenylmethyl-4-(trans-2-cyano-cyclopropyl)imidazole (200 mg, 0.54 mmol) and trifluoroacetic acid (TFA) (10 mL) was stirred at room temperature for 1–3 hours. The TFA was evaporated under reduced pressure. The resulting mixture was diluted with distilled water (5 mL) and extracted with ether (3×15 mL). The aqueous layer was lyophilized to give the product as a solid (73 mg, 55% yield).

Example 2

Preparation of 4-(trans-2-aminocarbonyl-cyclopropyl)imidazole trifluoroacetic acid salt A mixture of N-triphenylmethyl-4-(trans-2-cyano-cyclopropyl)imidazole (150 mg, 0.4 mmol) and concentrated hydrogen chloride (37%, 5 mL) was heated to 40° C. for 1.5 hours and then diluted with water (20 mL). The aqueous solution was extracted with ether (3×15 mL) and lyophilized to give the amide product (53 mg, 50% yield).

Example 3

Preparation of N-triphenylmethyl-4-(trans-2-amidino-cyclopropyl)imidazole

A solution of trimethylaluminium in toluene (2M, 0.6 mL, 1.2 mmol) was slowly added to a suspension of ammonium chloride (64 mg, 12 mmol) in dry toluene (5 mL) at 0° C. under nitrogen. The resulting mixture was warmed to 25° C. and stirred for 3 hours until gas evolution had ceased. Then, N-triphenylmethyl-4-(trans-2-cyano-cyclopropyl)imidazole (200 mg, 0.53 mmol) in dry toluene (10 mL) was added and the reaction mixture was heated to 80° C. for 18 hours under nitrogen, slowly poured into a slurry of silica gel (15 g) in chloroform (50 mL), and stirred for 10 minutes. The silica was filtered and washed with methanol. The combined solvent mixture was concentrated under vacuum and the residue was purified on a silica gel column using 85/15/5 (v/v/v) methylene chloride/methanol/ammonium hydroxide as the eluent to give a white solid (140 mg, 68% yield).

Preparation of 4-(trans-2-amidino-cyclopropyl) imidazole di-trifluoroacetic acid salt A mixture of N-triphenylmethyl-4-(trans-2-amidino-cyclopropyl)imidazole (100 mg, 0.26 mmol) and trifluoroacetic acid (TFA) (10 mL) was stirred at room temperature for 1–3 hours. The TFA was evaporated under reduced pressure, and the residue was diluted with distilled water (5 mL) and extracted with ether (3×10 mL). The aqueous layer was lyophilized to give the product as a solid (41 mg, 43% yield).

Example 4

Preparation of N-triphenylmethyl-4-(trans-2-aminomethyl-cyclopropyl)imidazole

To a solution of 2-[1-(triphenylmethyl)imidazol-4-yl] cyclopropanecarbonitrile (200 mg, 0.53 mmol) in dry diethyl ether (20 mL) was added lithium aluminum hydride (40 mg, 1.05 mmol) portion-wise at 0° C. under nitrogen. The reaction was stirred for 9 hours at room temperature. Water (0.5 mL) was added followed by the addition of a 15% sodium hydroxide solution (2.0 mL). The mixture was extracted with ethyl acetate. The organic layer was dried with $MgSO_4$ and concentrated. The resulting residue was eluted through a silica gel column using $CH_2Cl_2$/MeOH/$NH_4OH$ (85:15:5) to give a white solid amine product (130 mg, 65% yield).

Preparation of 4-(trans-2-aminomethyl-cyclopropyl) imidazole di-hydrochloric acid salt To a solution of N-triphenylmethyl-4-(trans-2-aminomethyl-cyclopropyl)imidazole (100 mg, 0.26 mmol) in methanol (15 mL) was added 2N HCl solution (2.5 mL). The mixture was stirred at 60° C. for 2 hours and then concentrated. The resulting residue was extracted with ether (3×20 ml). The aqueous layer was lyophilized to give the product (47 mg, 83% yield).

Example 5

Preparation of 4-(trans-2-hydrocarbonyl-cyclopropyl)imidazole

To a solution of N-triphenylmethyl-4-(trans-2-hydrocarbonyl-cyclopropyl)imidazole (1.0 g, 2.65 mmol) in methanol (20 mL) was added 2N HCl (3 mL). The mixture was stirred at 60° C. for about 2 hours and concentrated under reduced pressure. The reaction mixture was then diluted with water (50 mL), and its pH was adjusted to 8.0 with saturated potassium carbonate solution. The resulting mixture was saturated with sodium chloride and then extracted with ethyl acetate (3×50 mL). The organic layer was dried with sodium sulfate and the solvent was evaporated to give a yellow oil (0.3 g, 82% yield).

Preparation of 4-(trans-2-N-hydroxyimino-cyclopropyl)imidazole

To a solution of hydroxylamine hydrochloride (115 mg, 1.6 mmol) and 4-(trans-2-hydrocarbonyl-cyclopropyl) imidazole (150 mg, 1.6 mmol) in acetonitrile was added triethylamine (0.24 mL, 1.6 mmol). The mixture was stirred at room temperature for about 2 hours to give a precipitate, which was filtered. The filtrate was concentrated under vacuum and the residue was purified on a silica gel column, using a mixed solvent of $CH_2Cl_2$/MeOH/$NH_4OH$ (85:15:5) to give the title product (103 mg, 43% yield).

Example 6

Preparation of N-triphenylmethyl-4-(trans-2-hydroxymethyl-cyclopropyl)imidazole trifluoroacetic acid salt To a solution of N-triphenylmethyl-4-(trans-2-hydrocarbonyl-cyclopropyl)imidazole (200 mg, 0.53 mmol) in dry diethyl ether (20 mL) was added lithium aluminum hydride (40 mg, 1.05 mmol) at 0° C. under nitrogen. The reaction was stirred for 12 hours at room temperature, and water (0.5 mL) was added followed by the addition of 15% sodium hydroxide solution (2.0 mL). The reaction mixture was extracted with ethyl acetate. The organic layer was dried with $MgSO_4$ and concentrated under vacuum to give the product as a white solid (130 mg, 65% yield).

Preparation of 4-(trans-2-hydroxymethyl-cyclopropyl)imidazole trifluoroacetic acid salt A mixture of N-triphenylmethyl-4-(trans-2-hydroxymethyl-cyclopropyl)imidazole (100 mg, 0.26 mmol) and trifluoroacetic acid (TFA) (10 mL) was stirred at room temperature for 1–3 hours. The TFA was evaporated under reduced pressure. The resulting mixture was diluted with distilled water (5 mL) and extracted with ether (3×15 mL). The aqueous layer was lyophilized to give the product (61 mg, 93% yield).

Example 7

Preparation of N-triphenylmethyl-4-(trans-2-N-methylamidino-cyclopropyl)imidazole A solution of trimethylaluminium in toluene (2M, 0.54 mL, 1.08 mmol) was slowly added to a suspension of methylamine hydrochloride (73 mg, 1.08 mmol) in dry toluene (15 mL) at 0° C. under nitrogen. The resulting mixture was warmed to 25° C. and stirred for 3 hours until gas evolution had ceased. Then, N-triphenylmethyl-4-(trans-2-cyano-cyclopropyl)imidazole (200 mg, 0.53 mmol) in dry toluene (10 mL) was added, and the solution was heated to 80° C. for 18 hours under nitrogen. The reaction mixture was slowly poured into a slurry of 15 g of silica gel in chloroform (50 mL), stirred for 10 minutes, and filtered. The silica gel was further washed with methanol. The combined solvent was concentrated under vacuum to give a residue, which was purified on a silica gel column, using a mixed solvent consisting of methylene chloride/methanol/ammonium hydroxide 85/15/5 (v/v/v) as the eluent to give the N-methyl amidine product (89 mg, 45% yield).

Preparation of 4-(trans-2-N-methylamidino-cyclopropyl)imidazole di-hydrochloric acid salt To a solution of N-triphenylmethyl-4-(trans-2-N-methylamidino-cyclopropyl)imidazole (55 mg, 0.15 mmol) in methanol (15 mL) was added 2N HCl solution (2.5 mL). The mixture was stirred at 60° C. for 2 hours and then concentrated. The resulting residue was extracted with ether (3×15 mL), and the aqueous layer was lyophilized to give the final product (25 mg, 74% yield).

Example 8

Histamine $H_3$ receptor affinity was determined in rat cerebral cortical membranes with [$^3$H]NAMHA as previously described (Tedford et al., 1995). Animals were euthanized by rapid decapitation and cerebral cortical tissues were harvested and frozen on dry ice. Cerebral cortical membranes were prepared in 50 mM sodium-phosphate buffered saline (pH 7.5 at 4° C.) containing: EDTA (10 mM), phenylmethylsulfonyl fluoride (0.1 mM), chymostatin and leupeptin (each 0.2 mg/50 mL). The final membrane pellets were resuspended in water and stored frozen at −80° C. prior to use. Protein concentrations were determined using the Coomassie Plus Protein Assay (Pierce, Rockford Ill.).

Competition binding was carried out in a total volume of 0.2 mL of 50 mM sodium-phosphate buffer (pH 7.4) using ~1 nM [$^3$H]NAMHA ([$^3$H]—N$^\alpha$-methylhistamine, available from NEN Research Products of Boston, Mass.) and 0.003 to 10,000 nM concentrations of the test compounds. Non-specific binding was determined using 10 μM thioperamide. Samples were incubated for 40 minutes at 25° C. and subsequently filtered through Whatman GF/C glass fiber filters pre-soaked in binding buffer with 0.3% polyethyleneimine, using an Inotech cell harvester (Inotech Biosystems International, Lansing Mich.). The filters were rapidly washed three times with Tris-NaCl buffer (25 and 145 mM, respectively, pH 7.4, 4° C.). Samples were quantitated using Ecolume scintillation cocktail (ICN Biomedicals; Costa Mesa Calif.) and a Packard model 1900TR liquid scintillation analyzer (Packard Instrument Co., Downers Grove Ill.). IC$_{50}$ values were extrapolated from a plot of receptor occupancy (i.e. % bound) vs. log [competitor]. Inhibition constants (K$_i$'s) were determined using the equation: K$_i$=IC$_{50}$/(1+([ligand]/[K$_d$]), where K$_d$=0.4 nM for [$^3$H] NAMHA. In Table 1, a lower K$_i$ value for binding of the competitive ligand indicates that the tested compound has greater affinity for histamine H$_3$ receptors.

TABLE I

| Example # | Name | NMR Data | Ki (nM) |
|---|---|---|---|
| Example 1 | 4-(trans-2-cyano-cyclopropyl)imidazole trifluoroacetic acid salt | δ 8.81(s, 1H), 7.42(1, 1H), 2.75 (m, 1H), 2.0(m, 1H), 1.74(m, 1H), 1.59(m, 1H) | 20 |
| Example 2 | 4-(trans-2-aminocarbonyl-cyclopropyl)imidazole trifluoroacetic acid salt | δ 8.80(s, 1H), 7.25(s, 1H), 2.55(m, 1H), 2.0(m, 1H), 1.55(m, 1H), 1.35(m, 1H) | 127 |
| Example 3 | 4-(trans-2-amidino-cyclopropyl)imidazole di-trifluoroacetic acid salt | δ 8.84(s, 1H), 7.45(m, 1H), 2.8(m, 1H), 2.23(m, 1H), 1.9(m, 2H). | 6.7 |
| Example 4 | 4-(trans-2-aminomethyl-cyclopropyl)imidazole di-hydrochloric acid salt | δ 8.79(s, 1H), 7.35(s, 1H), 3.12(m, 1H), 2.97(m, 1H), 2.10(m, 1H), 1.54(m, 1H), 1.20(m, 2H) | 4.5 |
| Example 5 | 4-(trans-2-N-hydroxymethyl-cyclopropyl)imidazole | δ 7.68(m, 1H), 7.05(d, J=26 Hz, H), 6.84(d, J=13 Hz, 1H), 2.50(m, 1H), 2.17(m, 1H), 1.30(m, 1H). | 23 |
| Example 6 | 4-(trans-2-hydroxymethyl-cyclopropyl)imidazole trifluoroacetic acid salt | δ 8.50(s, 1H), 7.15(s, 1H), 3.65(m, 1H), 3.55(m, 1H), 1.90(m, 1H), 1.51(m, 1H), 1.10(m, 2H). | 263 |
| Example 7 | 4-(trans-2-N-methylamidino-cyclopropyl)imidazole di-hydrochloric acid salt | δ 8.84(s, 1H), 7.55(m, 1H), 2.86(s, 3H), 2.75(m, 1H), 2.33(m, 1H), 1.87(m, 1H), 1.75(m, 1H). | 114 |

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A compound which is selected from the group consisting of:
    4-(trans-2-cyano-cyclopropyl)imidazole,
    4-(trans-2-aminocarbonyl-cyclopropyl)imidazole,
    4-(trans-2-amidino-cyclopropyl)imidazole,
    4-(trans-2-aminomethyl-cyclopropyl)imidazole,
    4-(trans-2-N-hydroxyimino-cyclopropyl)imidazole,
    4-(trans-2-hydroxymethyl-cyclopropyl)imidazole,
    4-(trans-2-N-methylamidino-cyclopropyl)imidazole,
    4-(trans-2-aminomethyl-2-methyl-cyclopropyl)imidazole,
    4-(trans-2-amidino-2-methyl-cyclopropyl)imidazole,
    and pharmaceutically acceptable salts thereof.

2. A pharmaceutical composition comprising a compound of claim 1 and a pharmaceutically acceptable carrier.

3. A method for the treatment of a disease or disorder selected from the group consisting of: allergy, cardiovascular disease, inflammation, hypotension, glaucoma, sleeping disorder, hypermotility of the gastrointestinal tract, hypomotility of the gastrointestinal tract, hypoactivity of the central nervous system, hyperactivity of the central nervous system, Alzheimer's disease, schizophrenia, obesity and migraine; which comprising administering to a mammal in need of such treatment an effective amount of the compound of claim 1.

* * * * *